(12) United States Patent
Thorpe et al.

(10) Patent No.: US 9,642,440 B2
(45) Date of Patent: May 9, 2017

(54) APPLICATOR DEVICE OR DISPENSER WITH STONE TIP

(71) Applicant: HCT ASIA LTD., Central (HK)

(72) Inventors: Timothy Thorpe, Santa Monica, CA (US); Armando Villarreal, Los Angeles, CA (US); Courtney Frances Haley, McIntosh, FL (US); Denis Pierre Maurin, Los Angeles, CA (US)

(73) Assignee: HCT ASIA LTD., Hong Kong (HK)

( * ) Notice: Subject to any disclaimer, the term of this patent is extended or adjusted under 35 U.S.C. 154(b) by 0 days.

(21) Appl. No.: 13/840,775

(22) Filed: Mar. 15, 2013

(65) Prior Publication Data

US 2014/0234010 A1    Aug. 21, 2014

Related U.S. Application Data

(60) Provisional application No. 61/766,645, filed on Feb. 19, 2013.

(51) Int. Cl.
*A45D 40/26* (2006.01)
*A61M 35/00* (2006.01)
*A45D 34/04* (2006.01)

(52) U.S. Cl.
CPC ............ *A45D 40/26* (2013.01); *A45D 34/04* (2013.01); *A45D 34/041* (2013.01); *A61M 35/003* (2013.01); *A45D 2200/1054* (2013.01); *A45D 2200/15* (2013.01); *A45D 2200/155* (2013.01)

(58) Field of Classification Search
CPC .......... A45D 2200/15; A45D 2200/155; A45D 2200/157
See application file for complete search history.

(56) References Cited

U.S. PATENT DOCUMENTS

| | | | | |
|---|---|---|---|---|
| 7,883,287 B2* | 2/2011 | Thorpe | .......................... | 401/266 |
| 7,959,369 B2* | 6/2011 | Gueret | .......................... | 401/123 |
| 8,161,983 B1 | 4/2012 | Lee | | |
| 2009/0062815 A1 | 3/2009 | Karasiuk | | |
| 2011/0103878 A1* | 5/2011 | Neuner et al. | ................ | 401/203 |

FOREIGN PATENT DOCUMENTS

FR    2758446 A1    7/1998
WO    89/12440 A1   12/1989

OTHER PUBLICATIONS

International Search Report mailed Apr. 22, 2014 in corresponding International Patent Application No. PCT/US2014/017020.

\* cited by examiner

*Primary Examiner* — Mark A Laurenzi
*Assistant Examiner* — Joshua Wiljanen
(74) *Attorney, Agent, or Firm* — Seager, Tufte & Wickhem LLP

(57) ABSTRACT

An applicator device or dispenser includes a stone applicator tip and a housing which may, in some examples, have a reservoir for containing a product, such as a cosmetics product or a medicinal product. The stone tip comprises a material that is capable of storing and retaining and/or transferring thermal energy during application of the product.

18 Claims, 13 Drawing Sheets

Figure 1:
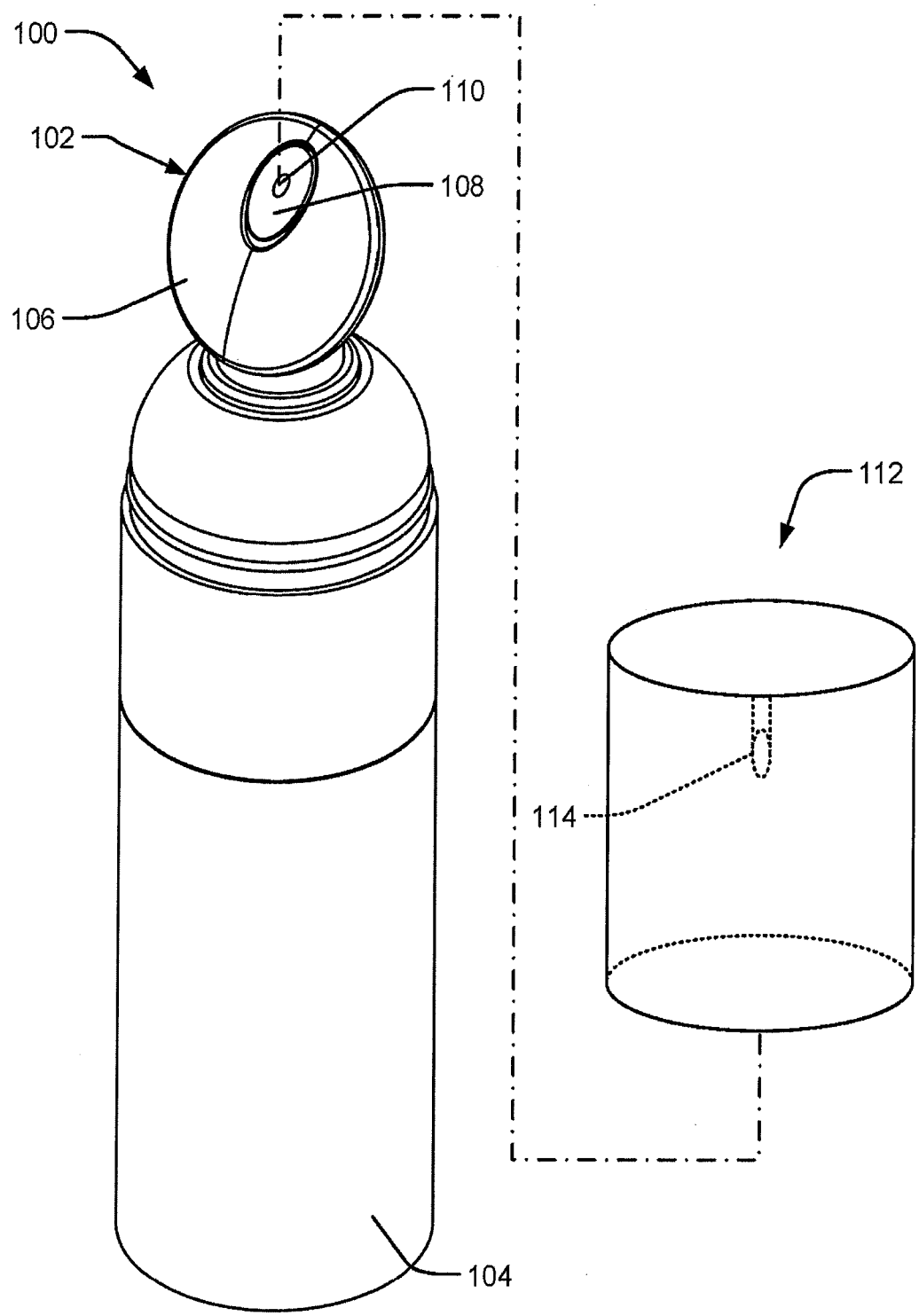

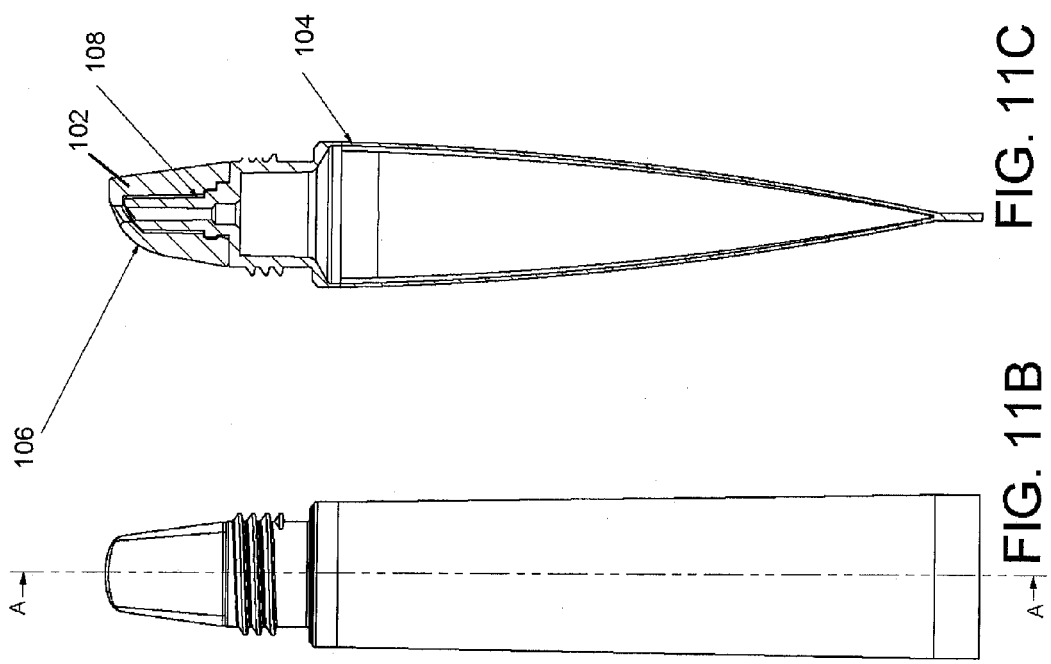
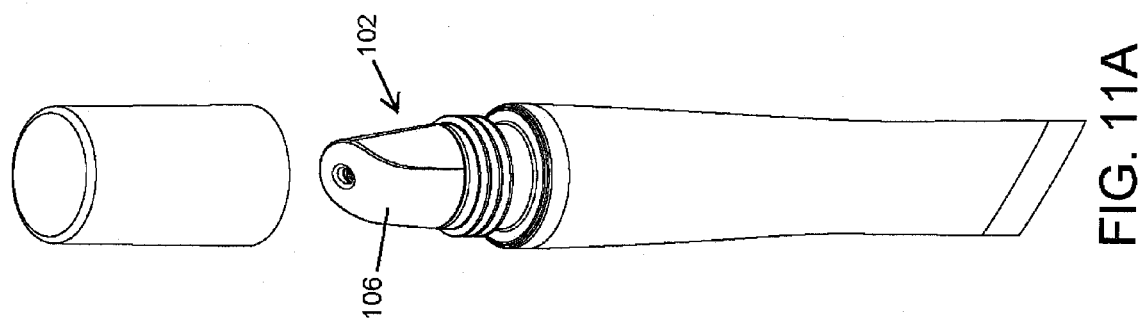
FIG. 11A  FIG. 11B  FIG. 11C

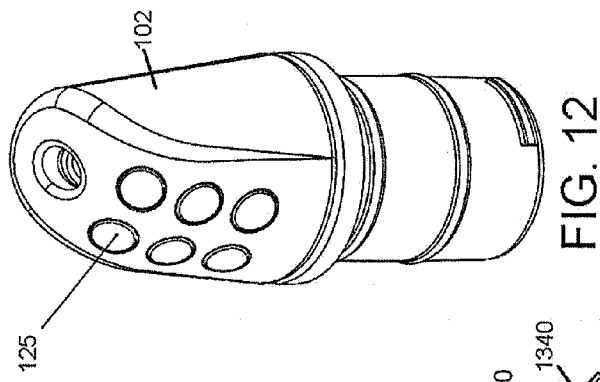
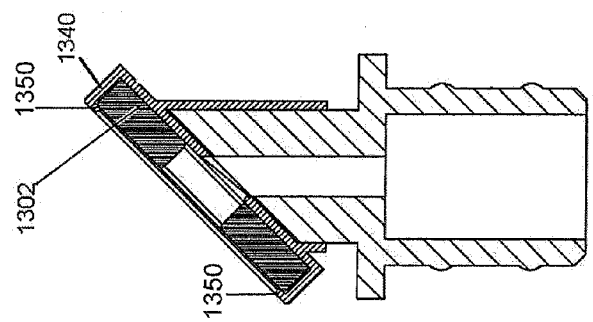
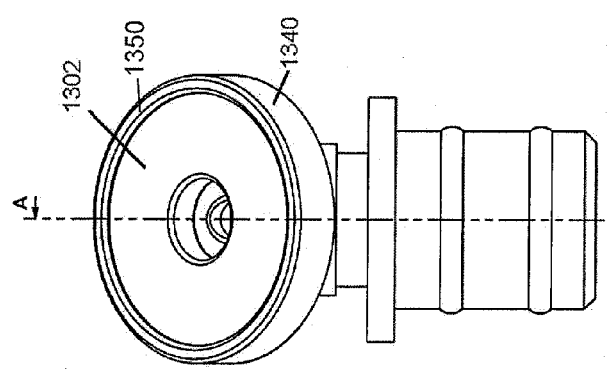
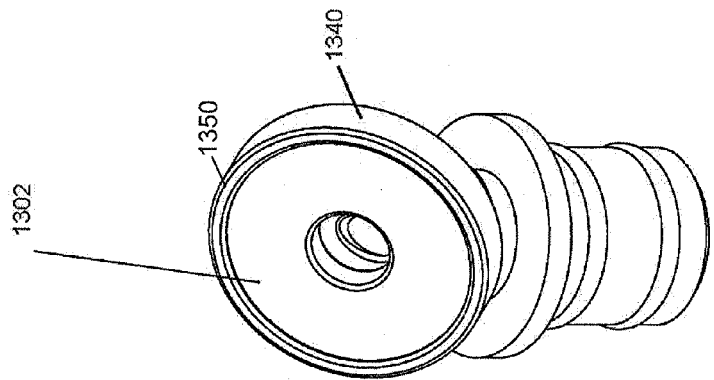

APPLICATOR DEVICE OR DISPENSER WITH STONE TIP

RELATED APPLICATION

This application claims priority to U.S. Provisional Patent Application No. 61/766,645, filed on Feb. 19, 2013, which is incorporated by reference herein.

BACKGROUND

Devices exist for dispensing cosmetic or medicinal products. Such devices usually consist of an outer tubular shell or housing, a delivery mechanism for displacement of the cosmetic or medicinal products, and an applicator tip. For example, in the medical industry, applicators are employed for applying medicinal products, such as ointments, to portions of the body. In the cosmetics and personal care industries, applicators are used to apply lipstick, lip balm, skin creams, lotions, and other cosmetic products to portions of the body.

In many cases, these medicinal and cosmetic products may include skin care substances, such as aloe or lanolin, that provide a healing or therapeutic effect to heal damaged skin or maintain healthy skin. In addition, these products may include therapeutic substances, such as topical anesthetics, analgesics, fragrances, menthol, or other substances that provide a soothing or stimulating sensation when applied to skin of a user of the product. In addition to skin care substances, thermal treatments (e.g., application of heat and/or cold) are known to relieve pain, provide a therapeutic sensation, and to slow the body's natural response to injury so that a slower and more controlled healing process may ensue.

Existing cosmetic and medicinal dispensers are limited to application of products to the skin, and do not provide for thermal treatments of the skin. Accordingly, there remains a need in the art for improved dispensers.

SUMMARY

This summary is provided to introduce simplified concepts of applicators and dispensers with stone applicator tips, which are further described below in the Detailed Description. This summary is not intended to identify essential features of the claimed subject matter, nor is it intended for use in determining the scope of the claimed subject matter.

This disclosure is directed to application devices, implements, or dispensers with stone applicator tips having thermal capacities, which are capable of storing and retaining thermal energy and/or transferring thermal energy. The stone applicator tips may allow a product to be applied locally or topically to a selected area of a surface.

In some implementations, a housing may be coupled to the stone applicator tip and may have a reservoir for product storage. The stone applicator tip may have an application face for applying the product to the user's skin.

In some implementations, the stone applicator tip may comprise a stone material capable of storing and retaining thermal energy and/or transferring thermal energy that can be heated or cooled and are able to retain or transfer the heated or cooled condition for a period of time.

In still further implementations, the stone applicator tips may include an insert or liner. The insert may be positioned generally in the center of the tip and may include a product delivery passageway extending through the stone applicator tip for dispensing a product to the application face.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 1 is a perspective view of an illustrative dispenser with a stone applicator tip according to one implementation;

FIG. 2 is a top view of the stone applicator tip of the dispenser of FIG. 1;

FIG. 3A is a cross-sectional view of the stone applicator tip of the dispenser shown in FIG. 1, taken along line A-A of FIG. 2;

FIG. 3B is a cross-sectional view of another illustrative embodiment of the stone applicator tip of the dispenser shown in FIG. 1, taken along line A-A of FIG. 2;

FIG. 4 is a cross-sectional view of the dispenser shown in FIG. 1, taken along line A-A of FIG. 2;

FIG. 5 is a front view of a stone applicator tip according to another illustrative implementation, in which the stone applicator tip is unitary;

FIGS. 6A and 6B are perspective and side views, respectively, of a stone applicator tip according to another illustrative implementation, in which the stone applicator tip includes a stone applicator;

FIGS. 6C and 6D are a side view and a cross-sectional view, respectively, of a stone tip according to still other illustrative embodiments in which the applicator tip includes a stone applicator;

FIGS. 7A-7C are perspective views of three other dispensers with stone applicator tips, according to other illustrative implementations;

FIG. 8A depicts a perspective view of one embodiment;

FIG. 8B depicts a front view of the embodiment depicted in FIG. 8A;

FIG. 8C depicts a cross-section view of the embodiment depicted in FIGS. 8A and 8B;

FIG. 9A depicts a perspective view of one embodiment;

FIG. 9B depicts a front view of the embodiment depicted in FIG. 9A;

FIG. 9C depicts a cross-section view of the embodiment depicted in FIGS. 9A and 9B;

FIG. 10A depicts a perspective view of one embodiment;

FIG. 10B depicts a front view of the embodiment depicted in FIG. 10A;

FIG. 10C depicts a cross-section view of the embodiment depicted in FIGS. 10A and 10B;

FIG. 11A depicts a perspective view of one embodiment;

FIG. 11B depicts a front view of the embodiment depicted in FIG. 11A;

FIG. 11C depicts a cross-section view of the embodiment depicted in FIGS. 11A and 11B;

FIG. 12 depicts an alternative embodiment having inlay material;

FIG. 13A depicts a perspective view of one embodiment having an annular ring surrounding a stone applicator;

FIG. 13B depicts a front view of the embodiment depicted in FIG. 8A; and FIG. 13C depicts a cross-section view of the embodiment depicted in FIGS. 13A and 13B.

DETAILED DESCRIPTION

Overview

This disclosure is directed to dispensers with stone applicator tips that are able to transfer and/or store and maintain a level of thermal energy. The stone applicator tips may comprise various stone materials, including but not limited to natural stone, synthetic stone, gemstone, imitation gemstone, glass stone, volcanic stone or composites thereof that are able to retain and/or transfer the heated or cooled condition for a period of time. More importantly, in some embodiments, due to the choice of materials and the relative size of the stone tip, the stone has the ability to convey a sensation of warming or cooling, and can regenerate that ability without external heating or cooling, other than exposure to ambient conditions. The stone applicator tip defines an application surface and a bore, through which product may be dispensed. A product may be dispensed from the dispenser through the stone applicator tip for application to a surface such as, for example, a user's skin. By virtue of the thermal retention or transfer of the tip, thermal energy may be applied to the dispensed product so that it may be heated or cooled during application. Moreover, the application face of the stone applicator tip may transfer heat to or from the user's skin, thereby causing the user to feel a thermal sensation (warm or cool depending on the thermal energy in or transferred via the stone applicator tip). In some cases, the heat or cold transfer may also minimize or alleviate pain or discomfort caused by damage to the skin or other surface.

In some embodiments, the stone applicator tip is coupled directly to a housing in others, a stone tip assembly is used, where the stone applicator tip is coupled to an insert which is coupled to the housing.

Those of skill in the art will readily recognize shaping techniques appropriate to the stone type. Thus, the stones may be shaped by any of cutting, carving, chipping, grinding, splitting, tumbling, polishing, binding, adhering, molding, bead blasting, etc., or any combination of these and other techniques.

Although the characteristics of the stone can vary depending upon the particular use, as noted above, the stone should have thermal storage capacity. In some embodiments, the stone is non-reactive to avoid chemical reaction between the stone and the product. In some embodiments, the stone is capable of being polished or otherwise treated to provide a smooth application surface. One of skill in the art developing such stone tips may ascertain a use for a tip having at least a portion of which is porous or more rough than the rest of the tip for various purposes, e.g., exfoliation. In most embodiments, however, a non-porous or relatively non-porous stone is desirable to avoid unwanted accumulation and waste of the product delivered.

Generally speaking, in most embodiments, the stone will be chosen because of its ability to convey a thermal property to the skin of the user. In most instances, the stone will convey a cooling sensation to the skin. Due to its thermal properties, size, and shape, the stone tip will convey this cooling sensation, in theory, by absorbing some heat from the user's skin. As the tip warms, the cooling property can be regenerated simply by removing the tip from the skin. A relatively quick return to ambient temperature will restore the stone's cooling capability. Of course, the stone will regain some of its cooling ability even before it returns to ambient temperatures. Other important properties of the stone include but are not limited to its size (mass and/or volume), surface characteristics, and its porosity.

While certain stone applicator tips are described herein as being capable of transferring or retaining heat or cold during the application of the product, in other embodiments stone applicator tips according to this disclosure need not necessarily be capable of capable of transferring or retaining heat or cold during the application of the product. For instance, stone applicator tips according to embodiments of this disclosure may completely or partially comprise a porous or aerated stone or aggregate material (e.g., pumice or other volcanic stone, aerated concrete, etc.).

According to some embodiments, stone applicator tips according to this disclosure may have a mass of stone of at least about 0.1 grams. According to certain other embodiments, stone applicator tips according to this disclosure may have a mass of at most about 10 grams. In some embodiments, stone applicator tips according to this disclosure may have a mass of from about 0.1 grams to about 0.5 grams; about 0.5 grams to about 1 gram; about 1 gram to about 5 grams and/or about 5 grams to about 10 grams. In some embodiments, the stone applicator tips disclosed herein may be about 0.1 grams, about 0.5 grams, about 1 gram, about 5 grams, or about 10 grams or any range between any two of these values. These ranges are merely exemplary and it is contemplated that even larger tips could be made with the principles disclosed herein, if desired.

According to certain embodiments, stone applicator tips according to this disclosure may have a volume of stone of at least about 0.1 centimeters$^3$. According to certain embodiments, stone applicator tips according to this disclosure may have a volume of stone of at most about 3 centimeters$^3$. In some embodiments, stone applicator tips according to this disclosure may have a volume of from about 0.1 centimeters$^3$ to about 0.3 centimeters$^3$; about 0.3 centimeters$^3$ to about 0.5 centimeters$^3$; about 0.5 centimeters$^3$ to about 0.7 centimeters$^3$; about 0.7 centimeters$^3$ to about 1 centimeter$^3$ about 1 centimeter$^3$ to about 2 centimeters$^3$, and/or about 1 centimeter$^3$ to about 3 centimeters$^3$. In some embodiments, the stone tip applicator has a volume of about 0.1 centimeters$^3$, about 0.3 centimeters$^3$; about 0.5 centimeters$^3$; about 0.7 centimeters$^3$; about 1 centimeter$^3$, about 2 centimeters$^3$, about 3 centimeters$^3$ and ranges between any two of these.

However, according to still other embodiments, stone applicator tips according to this disclosure may have masses and/or volumes of stone smaller or larger than those listed above. It should be further noted that based upon the choice of stone material and its density, a desired mass will yield a given volume, and conversely, a desired volume will yield a given mass. Nothing herein is to suggest that a chosen stone material will have a mass and volume inconsistent with its density. (Of course, composite materials or materials with air entrained within them will have a density unique to them and different from their individual components.)

In some embodiments, stone applicator tips may be subjected to one or more secondary or finishing operations, such as buffing, polishing, or chroming, for example. While features of various illustrative implementations are described, in other implementations, the storage tip may be configured in any form suitable for the application of the product to be dispensed. For example, the stone applicator tip may be constructed in any suitable shape and size and may have any suitable mass, volume, and/or surface treatment desired for a given application.

As used herein the term "stone" or "stone material" means any stone, rock, mineral, ore, gemstone, imitation gemstone, glass stone, volcanic stone or composites thereof whether naturally occurring or synthetic. For example, river stone is a naturally occurring stone that may be used in some embodiments.

Examples of suitable stone materials include, without limitation, imitation gemstone, glass stone, volcanic stone, choral stone, metallic stone or ore, magnetic stone, concrete, composites, or the like.

For purposes of this specification, the term "glass stone" is meant to include natural and man-made forms of glass.

Exemplary mineral gemstones include but are not limited to agate, alexandrite, amethyst, ametrine, apatite, aventurine, azurite, beintoite, beryl, bloodstone, carnelian, chrysoberyl, chrysocolla, citrine, diamond, diopside, emerald, falcon's eye, fluorite, garnet, heliotrope, hematite, hiddenite, iolite, jade, white jade, jasper, red jasper, labradorite, lapis lazuli, larimar, malachite, marcasite, moonstone, morganite, obsidian, onyx, opal, peridot, quartz, rock crystal, rose quartz, ruby, sapphire, selenite, sodalite, spinel, sunstone, tanzanite, tiger's eye, topaz, tourmaline, turquoise, yogo sapphire, and zircon. In some embodiments, one or more of diamond, hematite, jade, moonstone, rock crystal, ruby or sapphire may be used. In some embodiments, jade is used, including green jade, white jade, and/or colored jade in other embodiments, rock crystal may be used. Regardless of the choice of gemstone, any color or quality may be used.

Organic gemstones include but are not limited to abalone, amber, ammolite, copal, coral, ivory, jet, pearl, and nacre. In some embodiments, pearl may be used.

Synthetic gemstones include but are not limited to, cubic zirconia, moissanite, synthetic diamond, synthetic ruby, synthetic sapphire, synthetic emerald, and composite gemstones.

Stone, other than gemstones listed above, includes but is not limited to stone or rock such as soapstone, granite, marble, river rock, river stones, pebbles, metallic stone/ores (germanium for example), volcanic stone, engineered/composite stone, or synthetic stone.

Engineered, composite or synthetic stone can be made from one or more stones or stone powders which are bound together. As an example, concrete is made with aggregate stone material and binders. Concrete can be formed into many shapes via molding, cutting, grinding, etc., and even polished. Other engineered, composite, and synthetic stone is readily available, or can be custom made with stone materials of choice.

According to certain embodiments, the stone, or a plurality of stone materials, may be ground or crushed into a powder or an aggregate and then formed into a desired shape via, for example, injection molding or compression. The term "powder" is used herein with reference to relatively small particles, as opposed to "aggregate" which refers to relatively large particles. For our purposes here, both refer to smaller particles. According to certain embodiments, the powder may include granules having an average diameter of about 10 nm to about 10 micron. According to certain embodiments, an aggregate may include particles having an average diameter of at most about 10 millimeters. In some embodiments, the powder or aggregate may include granules having an average diameter from about 10 nm to about 150 microns; about 10 microns to about 10 millimeters; about 10 microns to about 100 microns; 100 microns to about 500 microns; 500 microns to about 1 millimeter; about 1 millimeter to about 5 millimeters; and/or about 5 millimeter to about 10 millimeters. In some embodiments, the powder or aggregates may include granules having an average diameter of about 10 nm, about 25 nm, about 50 nm, about 100 nm, about 150 nm, about 250 nm, about 500 nm, about 750 nm, about 1 micron, about 10 microns, about 25 microns, about 50 microns, about 100 microns, about 250 microns, about 500 microns, about 1 millimeter, about 2.5 millimeters, about 5 millimeters, and about 10 millimeters or any range of values between any two of these. However, in still other embodiments, the powder or aggregate may include granules larger or smaller than those listed. The granules may be of substantially uniform size (e.g., average diameter of about 25 microns, about 50 microns, about 250 microns, 2.5 millimeters, etc.) or size range (e.g., from about 25 microns to about 50 microns; 100 microns to about 250 microns, etc.), or the granules may include a variety of different sizes or size ranges. Moreover, the granules may be substantially uniform in shape (e.g., spherical, cubic, etc.) or may be non-uniform (e.g., randomly shaped crushed particles). Resins or other binders can be mixed with the ground stone to aid in the binding. Moreover, once the ground stone and resin/binder mixture has been molded, the resins or other binders may be removed via, for example, heat melting the resin or binder. According to certain embodiments, the stone can be coated or sealed with, for example, a polyurethane sealant, a lacquer, an ultraviolet (UV) inhibitor spray, a filler, or the like. According to still other embodiments, the stone can be polished (or roughed) to a desired surface finish.

Illustrative Dispenser with Stone Applicator Tip

FIG. 1 represents an illustrative dispenser 100 with a stone applicator tip 102 and a housing 104. In this implementation, the stone applicator tip 102 comprises a generally convex, disk-shaped applicator surface 106 made of a stone material capable of holding and retaining a thermal charge. It will be appreciated that any suitable shape can be used. In one implementation, the stone applicator tip 102 can be made of a gemstone such as, for example, jade. However, in other implementations, any suitable stone material may be used that is capable of transferring or retaining heat or cold during the application of the product.

Referring back to FIG. 1, the dispenser device 100 includes a generally cylindrical insert 108 extending from and in communication with the housing and at least partially through an aperture or bore in the stone applicator tip 102. Together, the aperture in the stone applicator tip 102 and the insert 108 define or form a product delivery passageway 110 for the product in housing 104. The product delivery passageway 110 communicates product from the housing 104 to the application surface 106 of the stone applicator tip 102. In some embodiments, the insert 108 extends substantially through the stone applicator tip 102, in others, the insert 108 extends only partially through the stone applicator tip 102, with the aperture in the stone applicator tip 102 completing the product delivery passageway 110. (see FIGS. 3A and 3B for a comparison). The insert 108 may be made of a thermoplastic polymer such as, for example, polypropylene, which is non-reactive with the product stored in the reservoir 104, and may be formed integrally with the housing or sealingly affixed thereto by methods known in the art.

The dispenser 100 may also include a cap 112 that encapsulates the stone applicator tip 102 when the dispenser is not in use and includes a plug 114 that seals the product delivery passageway 110. The plug 114 may be made of a thermoplastic polymer similar to insert 108 or any other material which is non-reactive or resistant to the product being dispensed, such as various metals, plastics, ceramics, composites, or the like. Additionally or alternatively, either the plug 114, the insert 108, or both may be elastomeric, such that when the cap is in place either the plug 114, insert 108, or both, may expand and deform somewhat to seal the product delivery passageway 110.

In some implementations, the stone applicator tip 102 may additionally include one or more other materials such as, for example, metal, plastic, glass, wood, carbon fiber, or the like. For instance, in some embodiments, metal, plastic, glass, wood, carbon fiber, or other material may be embedded in, on, or around a stone applicator 106. In one specific example, an applicator may include a stone tip with a metal ring around at least a portion of an outer perimeter of the stone tip. See FIGS. 12-13C.

Figure 2:
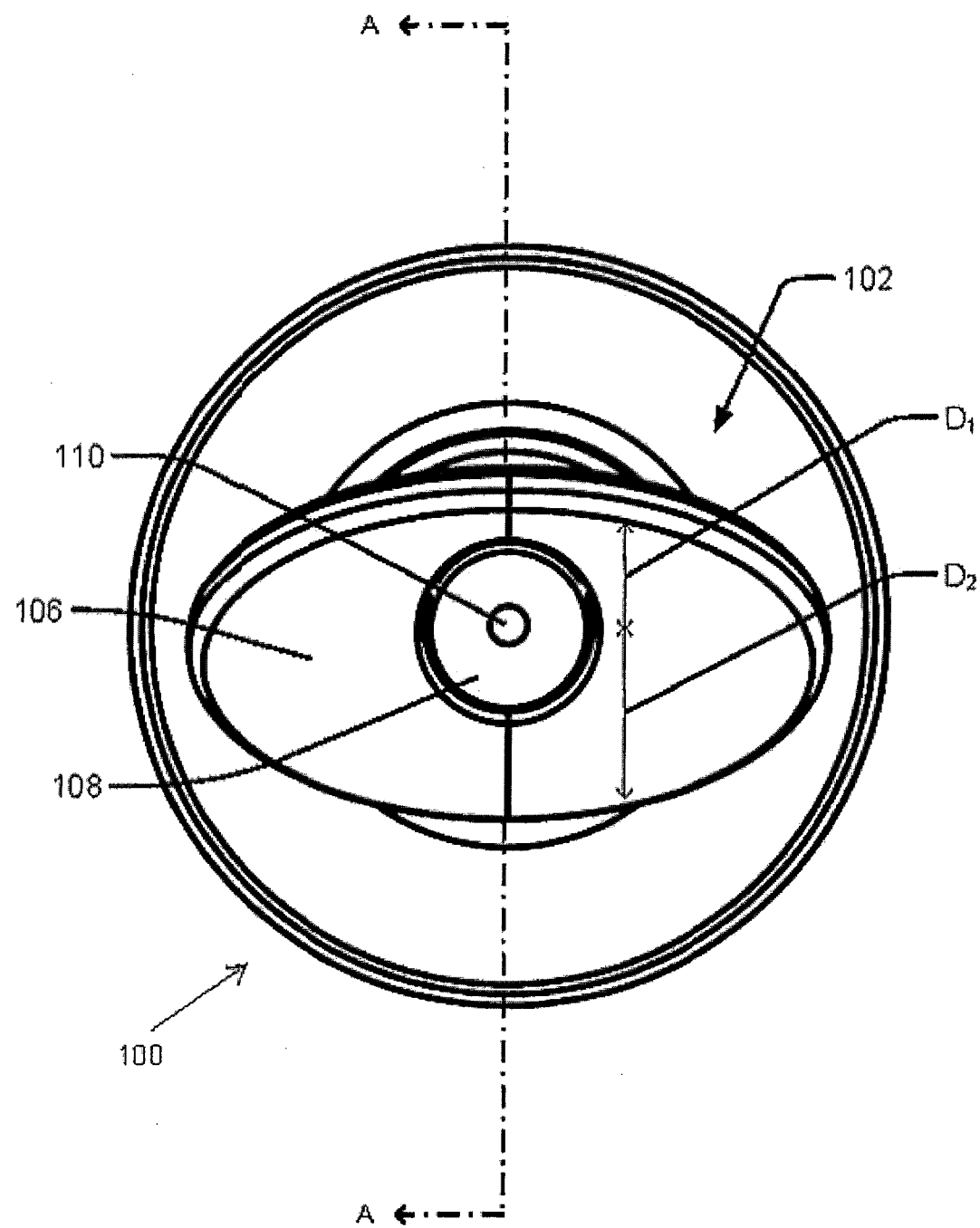

FIG. 2 is a top view of the stone applicator tip 102 of dispenser 100 in more detail. Again, the stone applicator tip 102 generally comprises the application face 106, and an aperture passing through the body of the applicator tip 102 to receive the insert 108, and thereby together define at least a portion of the product delivery passageway 110, which forms a dispensing path for the product in housing 104. In one implementation, the product delivery passageway 110 is positioned slightly off center within insert 108, when viewed along the longitudinal axis of the product delivery passageway. This is illustrated by the dimension lines $D_1$ and $D_2$ in FIG. 2, where $D_1$ is the distance from the topmost point of stone applicator tip 102 to the center of the product delivery passageway 110, and $D_2$ is the distance from the bottommost point of stone applicator tip 102 to the center of the product delivery passageway 100. As shown in the FIG. 2, $D_2$ is greater than $D_1$.

In one embodiment of this implementation, the stone applicator tip is shown as being a generally convex, disk-shaped body. FIGS. 7A-7C and 8A-8C show additional exemplary shapes. In addition, the stone applicator tip 102 in this implementation is made at least in part of stone. In some embodiments, the stone applicator tip is made from jade. In some embodiments using jade, the mass of stone is about 0.8 to about 2.5 grams. In some embodiments, the tip has a volume of from about 0.3 to about 0.7 centimeters$^3$. It is contemplated that any stone material, including jade, may be made in a variety of shapes and sizes. This description is merely illustrative of certain embodiments.

Figure 3A:
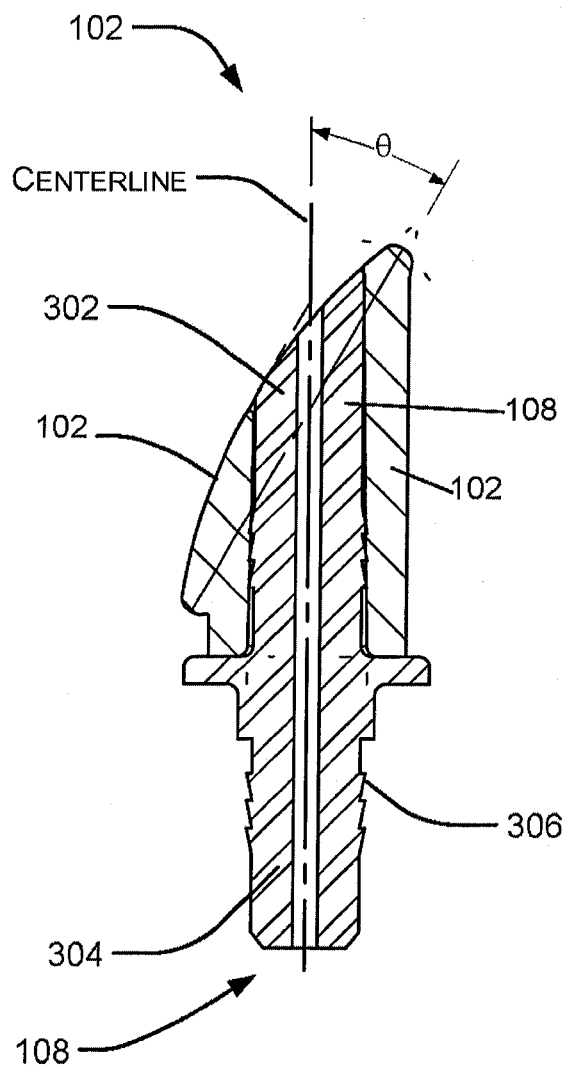

FIG. 3A shows an angle θ of the application face with respect to a centerline of the stone applicator tip. In the illustrated implementation, the angle θ is about 60°. This design facilitates application of the product to the user's skin. However, other designs may be used. For example, in other implementations the angle θ may be between about 30° and about 75°. According to certain embodiments, the application face may be articulable (e.g., pivotable, rotatable, etc.) such that the angle of the application face with respect to a centerline of the stone applicator tip can be changed by, for example, a user.

FIG. 3A also illustrates the construction of the stone applicator tip 102. As discussed above, the stone applicator tip 102 is a stone body that is capable of transferring and/or retaining thermal energy and defines an aperture for receiving an insert 108. The insert 108 includes a neck portion 302, which extends into the aperture in the stone applicator tip 102, and, in this embodiment, a connector stem 304 usable to retain the stone applicator tip 102 in the housing 104. The insert 108 may be secured to the stone applicator tip 102 and/or the housing 104 by, for example, a press-fit, snap-fit, adhesive, and/or engagement by one or more engagement features. In the illustrated implementation, the insert is retained in both the stone applicator tip and the housing 104 by a series of barbs or annular rings 306. FIG. 11 depicts an alternative embodiment where the insert 108 is affixed to the housing 104 as part of an end cap sealingly affixed to one end of the housing 104 to form a leak free seal between the insert and housing thereby directing product through the product delivery passageway 110 which is at least partially defined by the insert 108. In such a case, the insert 108 may be formed integrally with the housing such as by injection molding or affixed to the housing as is known in the art.

Figure 3B:
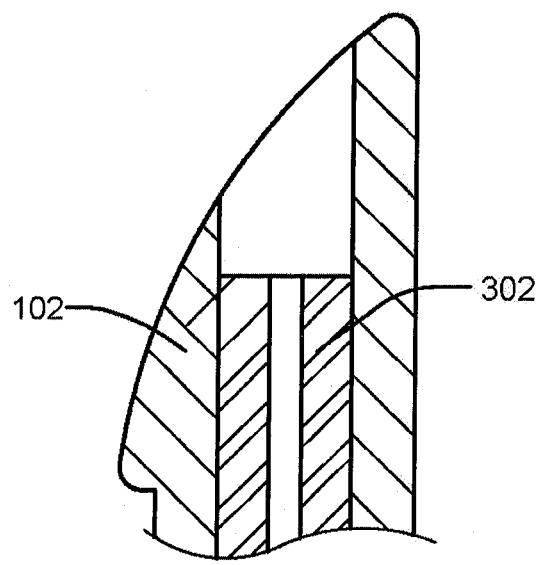

As shown in FIG. 3A, the insert 108 extends through the stone applicator tip 102 substantially to the upper most top of the stone applicator tip 102. In this embodiment, the insert 108 is substantially flush or even with the application surface 106. (The use of the term substantially is meant to account for minor differences, including those created by a chamfer or similar detent in the application surface.) In contrast, FIG. 3B illustrates another example embodiment of the dispenser device including a stone applicator tip 102 wherein the neck portion 302 of the insert 108 does not extend to the upper most top of the stone applicator tip thereby leaving a space between the top of the neck portion 302 and the top of the stone applicator tip 102. In this embodiment, the insert 108 is recessed from the application surface and the insert 108 and the aperture in the stone applicator tip together define the product delivery passageway.

Figure 4:
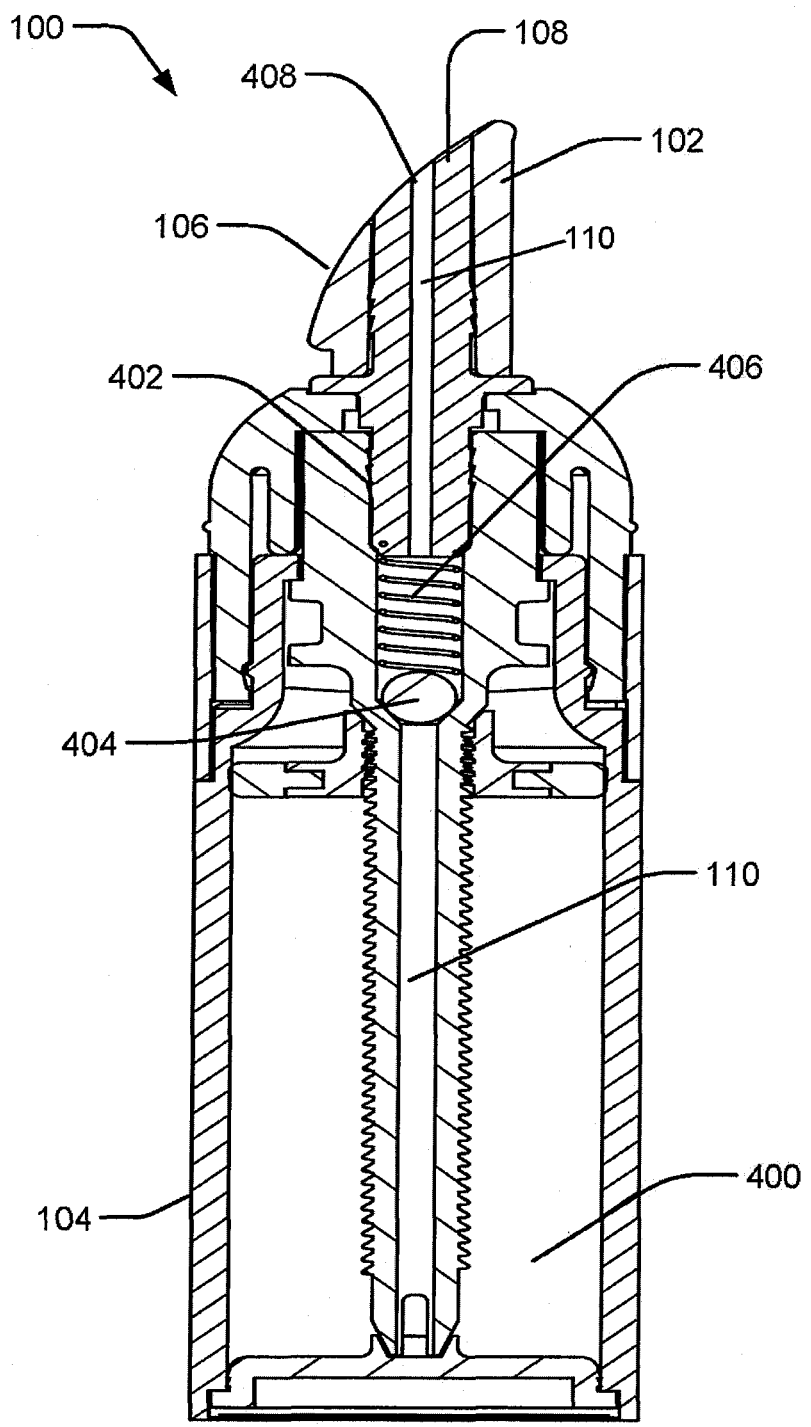

FIG. 4 is a cross-sectional view of dispenser 100, showing details of the housing 104. As shown in FIG. 4, the dispenser 100 has a reservoir 400. The product delivery passageway 110 extends from the reservoir 400, through at least part of the stone applicator tip 102 to provide product to an opening 408 in the application face 106. The product delivery passageway 110 may define all or part of a dispensing path from the reservoir to the application face 106. For instance, the product delivery passageway 110 may expel the product to the application face via a bore, recess, or other passage in the applicator 106 (the product delivery passageway 110 and the bore, recess, or other passage in the applicator collectively defining the dispensing path). In the illustrated implementation, the product is transported through the product delivery passageway 110 by rotating the housing 104 such that the product is dispensed through the stone applicator tip 102 by way of a check valve comprised of a ball 404 and a spring 406. However, in other implementations, any suitable delivery mechanism may be used.

The following is a discussion of examples, without limitation, of delivery mechanisms for dispensing a product. The first example may be implemented using a click or a reverse click operation, whereby the user may operate the dispenser by moving the applicator member relative to the housing member in either a clockwise or counterclockwise direction.

Another example delivery mechanism for dispensing the product may be a squeeze operation. In certain embodiments wherein the delivery mechanism is a squeeze operation, when pressure is applied to the housing containing the reservoir, the product in the reservoir may be forced, by the squeezing action, through the dispenser via a product delivery passageway for application to the user's skin.

In yet another example, a delivery mechanism for dispensing the product may be by a pressurized dispenser, such as an aerosol dispenser. In certain embodiments wherein the delivery mechanism is an aerosol delivery mechanism, the composition will be held under pressure in a container and will be dispersed along with an aerosol propellant in response to actuation by a user. Actuation may be by depressing, rotating, tilting, or otherwise manipulating the stone applicator tip, pressing a button, and/or by any other suitable dispensing mechanism. Details of the construction and propellant of an aerosol dispenser are within the skill of one of ordinary skill in the art and will, therefore, not be described in detail herein.

In yet another example, a delivery mechanism for dispensing product may be an airless pump. The term airless pump refers to a pump that provides dispensing of a substance from a container under pressure in essentially a single direction without permitting reverse (intake) flow of air via the pump. That is, as product is pumped from the container, the pumped product is not replaced with a corresponding volume of air through the pump. In addition to preventing reverse intake flow of air, an airless pump typically does not allow intake of any other substances to replace the volume of product pumped out of the container. For example, an airless pump could include a one-way valve, such as a check valve.

Further illustrated in FIG. 4, the stone applicator tip 102 is coupled to housing 104 by barbs located on a connector stem 402 of the stone applicator tip, which engage an interior of the housing 404. However, in other implementations the housing may be coupled to the stone applicator tip through any suitable means. Fabrication of housing 104 and stone applicator tip 102 may be accomplished through a separate manufacturing process, a co-molding process, or any other suitable production process.

FIGS. 9A-11C show, among other things, alternative housings, such as tubes or tottles. The type of housing is not linked or limited to a specific stone applicator tip or embodiment thereof. The different combinations shown in the figures is meant to be exemplary only. Any housing style can be used in conjunction with any stone applicator tip style. In these figures, the insert is affixed directly to the housing rather than through the use of barbs or other mechanical means.

Illustrative Unitary Stone Applicator Tip

While the dispenser 100 with a stone applicator tip 102 shown in FIGS. 1-4 includes an insert 108, in other implementations, the insert may be formed integrally with the body of the stone applicator tip, may be truncated, or omitted entirely. For example, where the product to be dispensed is not corrosive or otherwise reactive with the stone applicator tip (or for any other desired reason), the insert may be formed integrally with and of the same or different material as the stone applicator tip. In some instances, the insert will be omitted entirely. In that case, the stone applicator tip may consist of a unitary body with a dispensing path formed through the unitary body itself.

Figure 5:
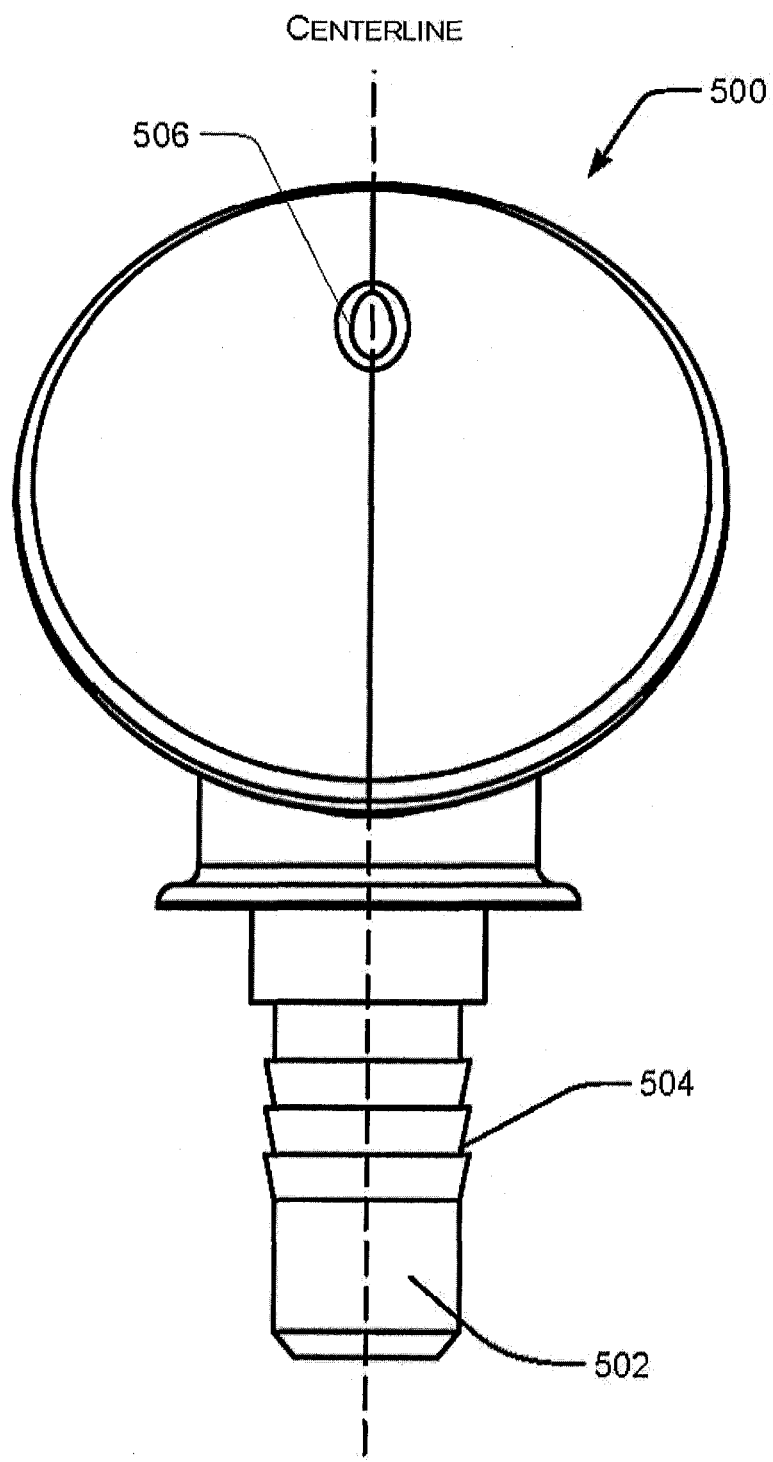
Figure 8C:
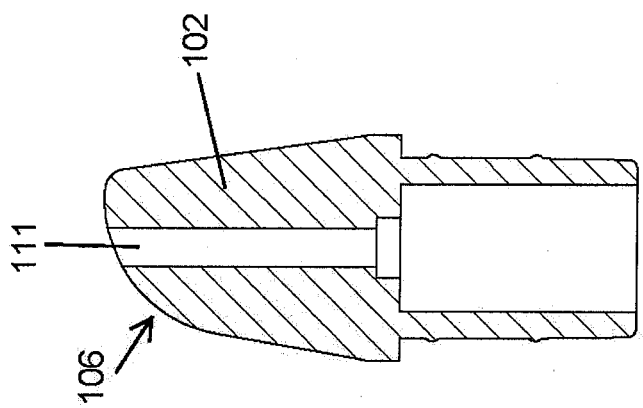
Figure 8B:
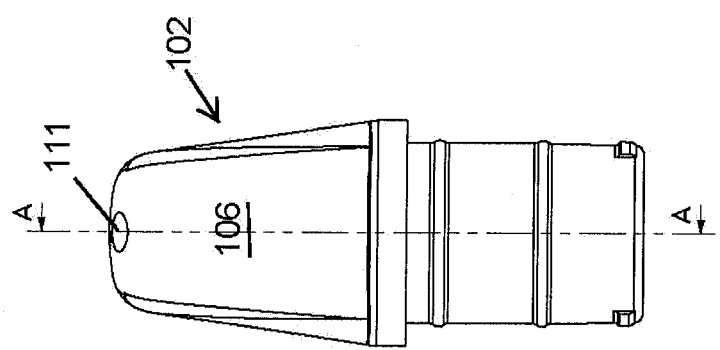
Figure 8A:
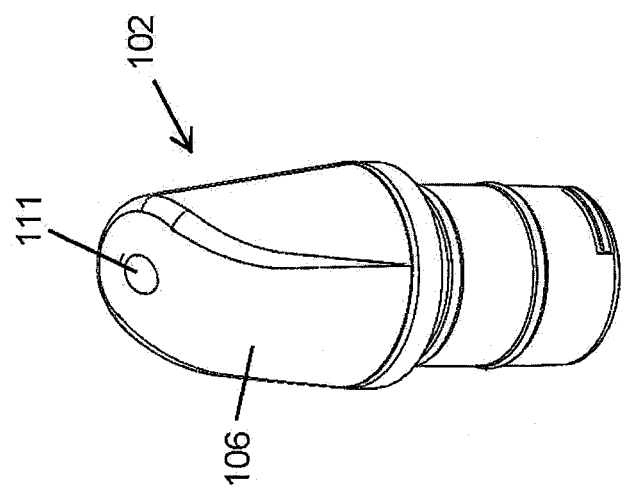

FIG. 5 shows an illustrative implementation in which a stone applicator tip 500 consists of a unitary body made of material capable of transferring and/or storing thermal energy. In this implementation, the stone applicator tip 500 includes a stem 502 with a series of barbs 504 configured to secure the tip 500 in a housing of a dispenser. A dispensing passageway 506 is formed through the interior of the stone applicator tip 500 to convey the product to be dispensed. In other respects, the stone applicator tip 500 is the same or similar to that shown in FIGS. 1-4. Accordingly, additional details of the applicator tip have been omitted for brevity. FIGS. 8A-8C depict an alternative shape, and include a cross-section, FIG. 8C, showing the bore 111 in the stone tip which defines the product delivery passageway. Of course, in embodiments employing an insert, the bore 111 would be capable of accepting the insert, and together define the product delivery passageway. FIGS. 8A-8C are shown with an insert for attaching to the housing. In other embodiments, the tip may be coupled to the housing by other means or methods.

Additional Example Applicator Devices with Stone Applicator Tips

Figures 6A, 6B:
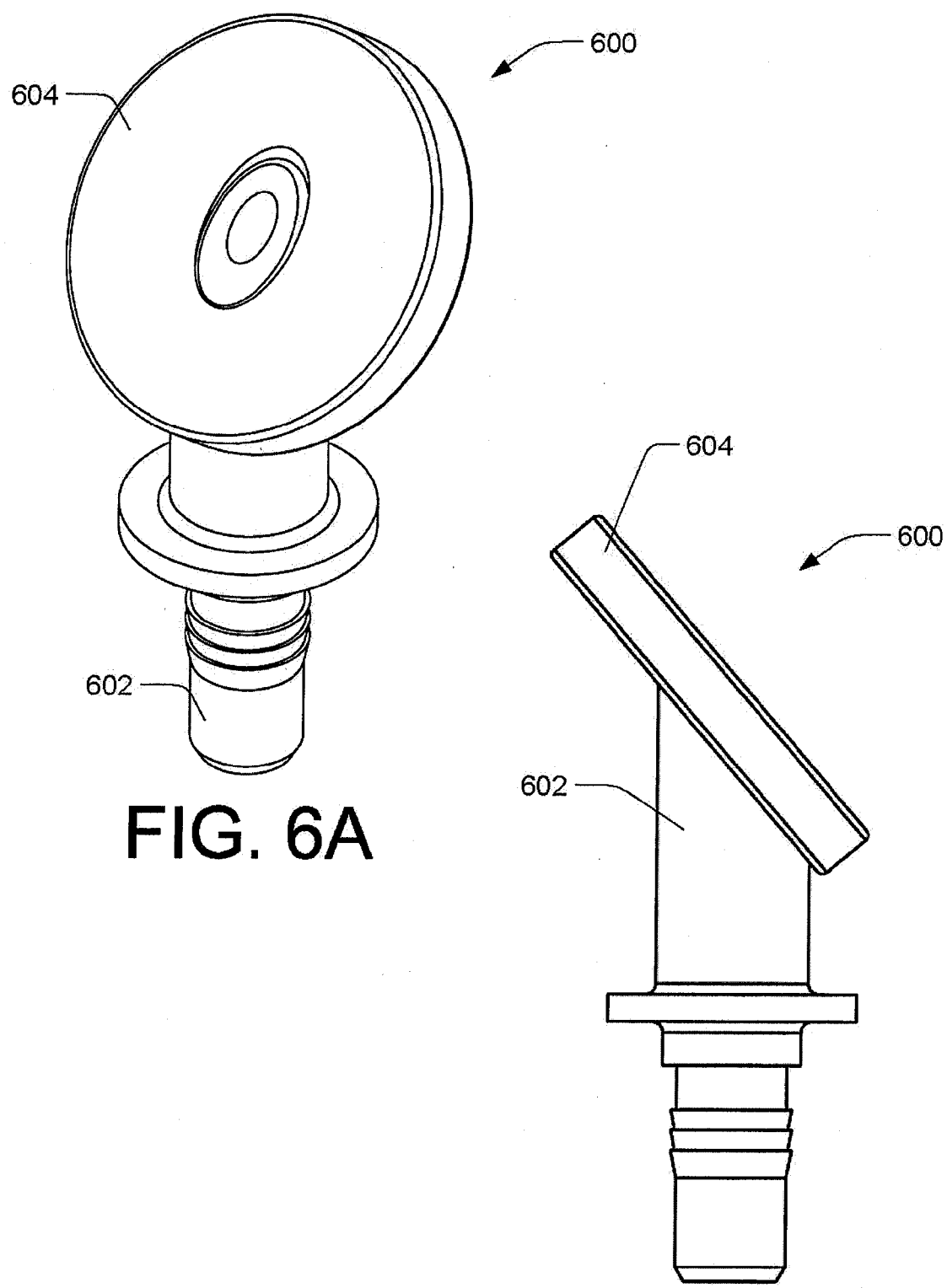

FIGS. 6A and 6B illustrate a stone applicator tip 600 according to yet another illustrative implementation. In this implementation, a stone applicator assembly 600 comprises a body 602 constituting a majority of the applicator tip, and stone applicator 604 coupled to the body 602. The body 602 may comprise, for example, plastic, metal, glass, or any other suitable material. The applicator 604 comprises a relatively thin member made of stone material. In this embodiment, the applicator 604 is illustrated as being generally disk- or ring-shaped.

Figure 6C:
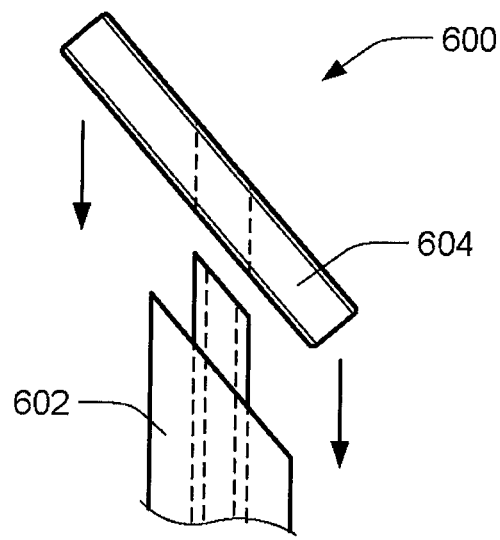

FIG. 6C illustrates an implementation in which the applicator 604 comprises a relatively thin, solid disk or ring of stone that is coupled to the body 602 by press fit. Additionally or alternatively, the applicator 604 may be coupled to the body by, for example, adhesive, snap fit, one or more ribs or barbs, or any other suitable fastening means. As will be appreciated, the body 602 forms a support for the stone applicator 604, regardless of its shape.

Figure 6D:
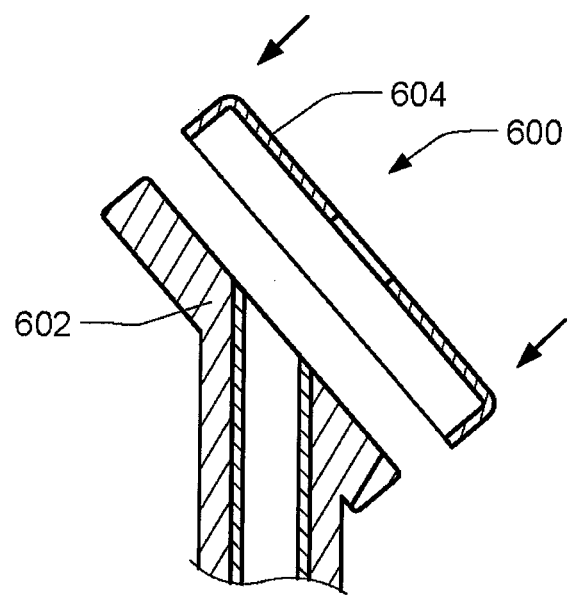
Figure 10C:
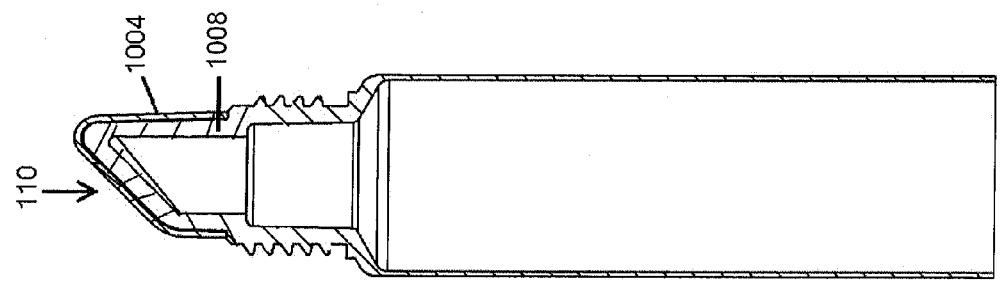
Figure 10B:
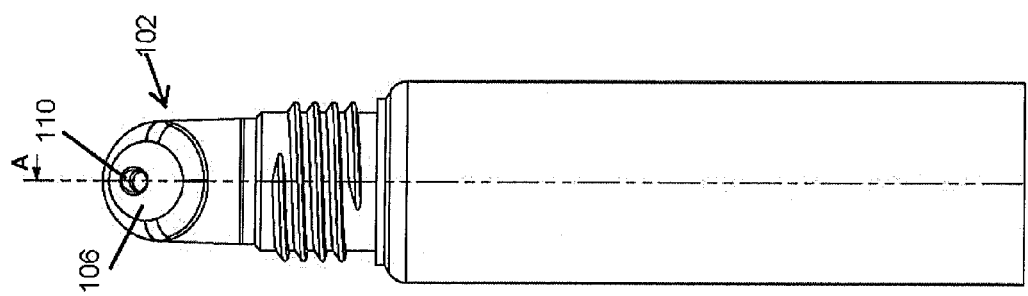
Figure 10A:
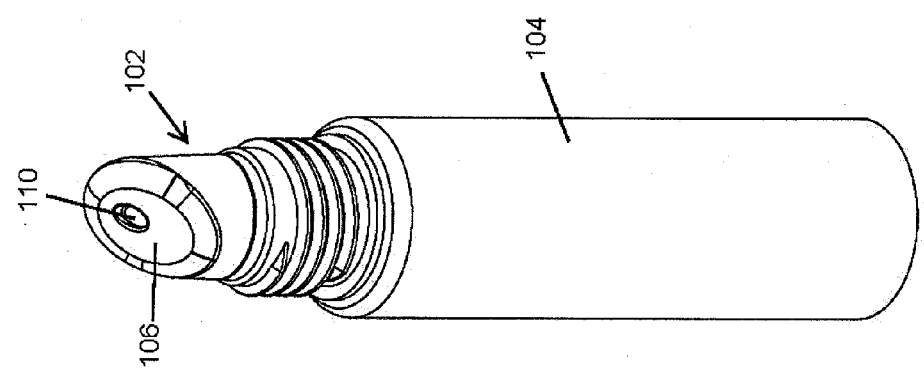

FIG. 6D illustrates an implementation in which the applicator 604 comprises a relatively thin cap or shell that is sized and shaped to fit over the top of the body 602. In practice, the body 602 and applicator 604 may be configured in virtually any desired shape, such as convex, disk-shaped, oval, elliptical, spherical, curvilinear, trapezoidal, or the like. In embodiments in which the applicator 604 comprises a relatively thin shell of stone, the shell of stone may be machined and pressed onto the body, or the stone may be in aggregate form and molded around the body, for example. A further embodiment having a relatively thin cap or shell is depicted in FIGS. 10A-10C. As seen in FIGS. 10A and 10B from all outward appearances the applicator resembles others. Cross-section FIG. 10C, however, shows the relatively thin shell 1004 over the body 1008.

In one example the embodiments of FIGS. 6A-6D, the applicator 604 may have a mass of stone of from about 0.1 grams to about 1 gram and a volume of stone from about 0.1 centimeters$^3$ to about 0.5 centimeters$^3$. However, in other examples, the applicator 604 may have volumes and/or masses larger or smaller than the examples given.

Alternative Illustrative Dispenser with a Stone Applicator Tip

In the implementations shown in FIGS. 1-6D, the stone applicator tip is shown as having a generally convex (FIGS. 1-5) or flat (FIGS. 6A and 6B), disk-shaped body. However, in other implementations, stone applicator tips may take any other desired form, such as generally spherical, elliptical, curvilinear, parabolic, flat, trapezoidal, combinations of the foregoing, or the like. Some exemplary alternatives are shown in FIGS. 7A-7C, and FIGS. 8A-12.

Figure 7A:
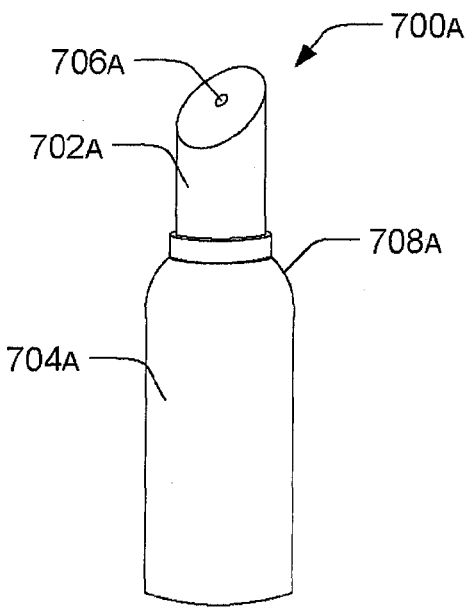
Figure 7B:
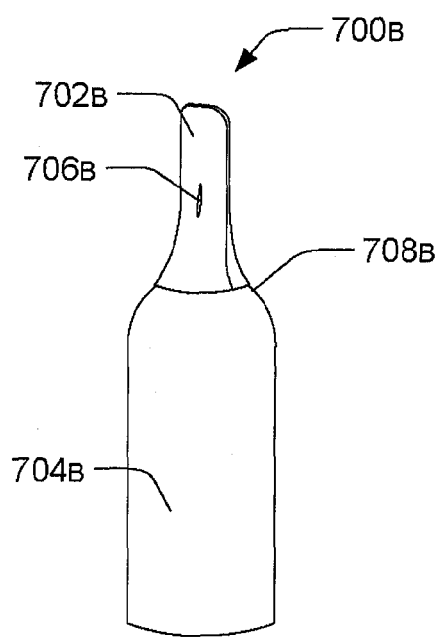
Figure 7C:
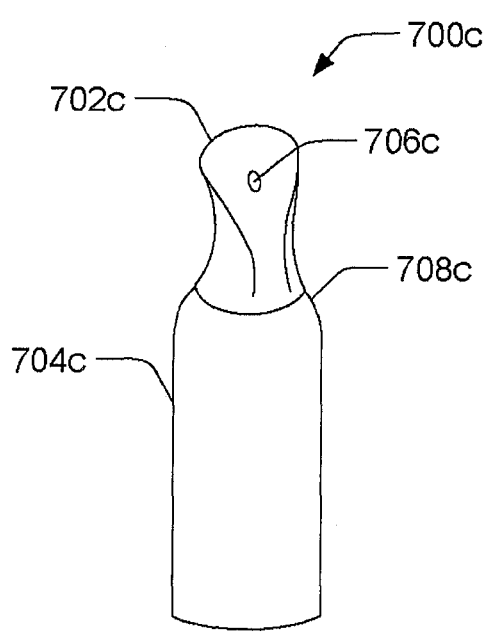

FIGS. 7A-7C show several alternative dispensers 700a-700c with various configurations and shapes of stone applicator tips. The dispensers 700a-700c shown in these implementations each include a stone applicator tip 702a-702c and a housing 704a-704c with a reservoir. In particular, the housings 704a-704c shown in these implementations are flexible tubes that may be squeezed to dispense product from a dispensing path 706a-706c through the stone applicator tip 702a-702c.

The stone applicator tips 702a-702c may be coupled to the respective housings 704a-704c by placing them over a narrowed neck 708a-708c of the housing and attaching them to the housing 704a-704c by, for example, crimping, adhesive, press-fit, snap-fit, retaining ribs or barbs on the inside of the stone applicator tip and/or the outside of the narrowed neck of the housing, and/or by any other suitable attachment means.

In still other implementations, dispensers may additionally or alternatively include a brush, a sponge, or various other features to assist in the application of a dispensed product to a user's skin.

While the dispensers with stone applicator tips shown in the figures are comprised of a separate applicator tip and housing, in other implementations to decrease manufacturing costs, or for any other desired reason, the applicator tip and some or all of the housing may be formed integrally. In still other implementations, application devices or implements may be configured with a stone applicator to apply cosmetic product, while omitting a reservoir for holding the cosmetic product. For instance, such an application device or implement may be dipped in a pot or reservoir of product to pick up the product for application to the skin or other surface.

Figure 9C:
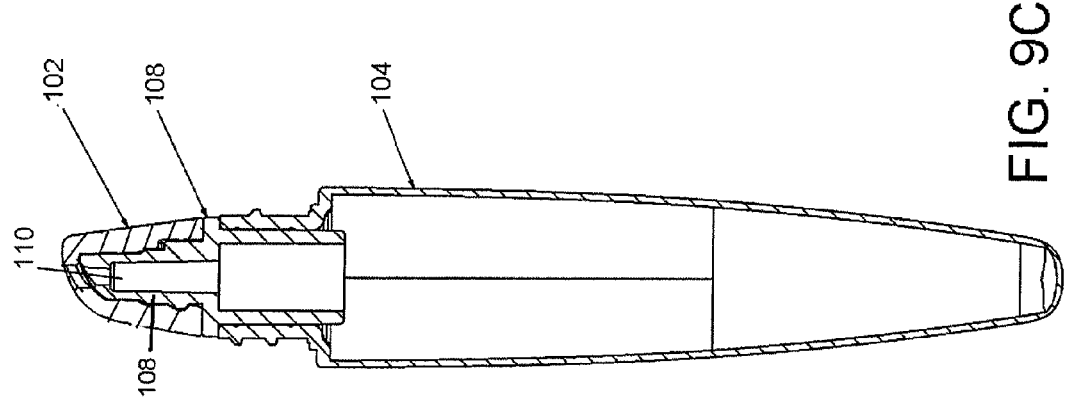
Figure 9B:
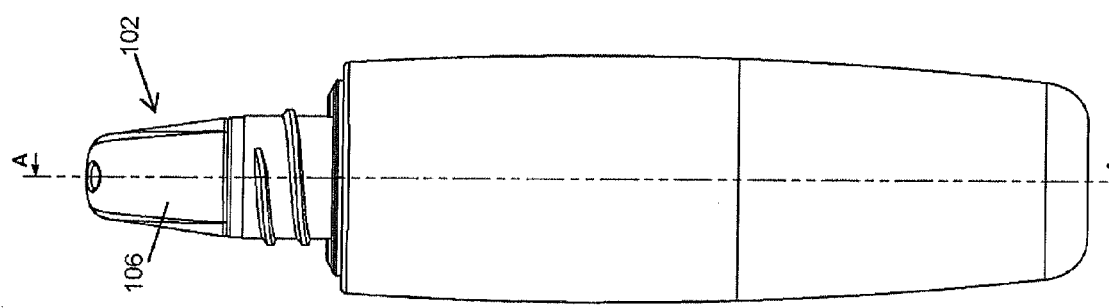
Figure 9A:
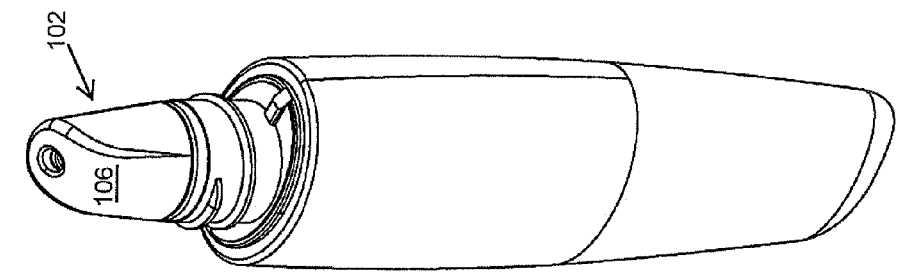

FIGS. 9A-9C show yet another alternative arrangement in this arrangement, the housing is a tottle (combination of tube and bottle common in the cosmetics industry). With respect to the applicator, a stone applicator tip 102 is provided. As described above, the stone applicator tip 102 defines an application surface 106 and a bore. In this embodiment, an insert 108 is provided which is in fluid communication with the housing. The insert 108 extends into the bore of the stone applicator tip 102 which together define the product delivery passageway 110 for conveying product from the housing to the application surface 106. In this, and similar arrangements, a tip assembly comprises the stone applicator tip 102 and the insert 108, which are made separately and later assembled. In some instances, the insert is coupled to the housing and the stone applicator tip 102 is subsequently applied.

FIGS. 10A-10C show another exemplary embodiment. In this instance, a tip assembly includes a stone applicator tip in the form of a relatively thin cap or shell 1004 which is coupled to a relatively large body 1002. The body 1002 may be formed integrally with the housing or coupled thereto similar to the insert of other embodiments.

FIGS. 11A-11C show yet another embodiment. A tube is used as the housing, and an insert 108 is coupled thereto. In this instance, the insert 108 is affixed to the housing in a finishing operation where the insert 108 is injection molded onto an extruded tube. The tube is subsequently filled and sealed. The stone applicator tip 102 as with other embodiments, includes an application face 106, and a bore for accepting an insert.

FIGS. 12 and 13A-C show alternative embodiments combining materials with the stone material. In addition to aggregates and engineered stone, the tip may include additional materials for decorative, aesthetic or useful purposes. FIG. 12 shows a stone applicator tip 102 having a plurality of inlays 125. The inlays 125 may be of any suitable material, other stone, the same stone (maybe in a different color or pattern), wood, plastic, metal, etc. Although referred to as inlays here, they could take any form, inlays, surface adornments, etc. They may be recessed, flush, or protruding. The inserts may be singular in nature or plural.

FIGS. 13A-C shows an embodiment including an annular ring 1340. In some embodiments, ring 1340 may be decorative. In others, it may form a tip holder, as shown particularly in FIG. 13C. In such embodiment, the annular ring 1340 is formed to hold the stone applicator in position. FIG. 13C depicts the annular ring 1340 as having crimped edges 1350 for holding the stone applicator 1302 in place.

It should be appreciated, particularly with the use of gemstones, that a jewelry like setting could be used in any embodiment to secure the stone to the insert and/or housing.

CONCLUSION

Although the invention has been described in language specific to structural features and/or methodological acts, it is to be understood that the invention is not necessarily limited to the specific features or acts described. Rather, the specific features and acts are disclosed as illustrative forms of implementing the invention.

What is claimed is:

1. A cosmetic application device comprising:
    a housing for containing product; and
    a stone applicator tip coupled to the housing, the stone applicator tip having a generally convex application surface having an angle θ between 35° and 75° with respect to a centerline of the stone applicator tip for applying a cosmetic or medicinal product to a surface, and a bore therethrough for communicating product from the housing to the generally convex application surface;
    wherein the stone applicator tip is shaped from a singular piece of stone material; and
    wherein the stone material comprises soapstone, granite, marble, river rock, river stones, pebbles, metallic stone/ores, volcanic stone, engineered/composite stone, or synthetic stone, or composites thereof, whether naturally occurring or synthetic.

2. The cosmetic application device of claim 1, wherein the stone material comprises soapstone, granite, marble, or river stone.

3. The cosmetic application device of claim 1, further comprising:
    an insert for placement extending into the bore of the stone applicator tip wherein the insert at least partially defines a product delivery passageway for delivering a cosmetic product from the housing to the generally convex application surface of the stone application tip.

4. The cosmetic application device of claim 3, wherein the insert comprises a thermoplastic polymer.

5. The cosmetic application device of claim 1, wherein the stone material comprises marble.

6. A cosmetic application device comprising:
    a housing for containing product; and
    a stone applicator tip coupled to the housing, the stone applicator tip having a generally convex application surface having an angle θ between 35° and 75° with respect to a centerline of the stone applicator tip for applying a cosmetic or medicinal product to a surface, and a bore therethrough for communicating product from the housing to the generally convex application surface;
    wherein the stone applicator tip is shaped from a singular piece of stone material, wherein the stone applicator tip comprises engineered stone that has been molded to thereby form the applicator tip.

7. The cosmetic application device of claim 6, wherein the engineered stone comprises marble.

8. A product dispenser tip assembly comprising:
    a stone applicator tip defining a bore therethrough and further defining a generally convex application surface having an angle θ between 35° and 75° with respect to a centerline of the stone applicator tip for applying a product; wherein the stone applicator tip is shaped from a singular piece of stone material; and an insert for extending into the bore of the stone applicator tip and further adapted for communication with a housing containing product;

wherein the bore in the stone applicator tip and the insert combine to define a product delivery passageway;

wherein the stone material comprises soapstone, granite, marble, river rock, river stones, pebbles, metallic stone/ores, volcanic stone, engineered/composite stone, or synthetic stone, or composites thereof, whether naturally occurring or synthetic.

9. The product dispenser tip assembly of claim 8, wherein the stone material comprises marble.

10. A dispenser comprising:

a housing having a reservoir for containing a product; and a stone applicator tip coupled to the housing, the stone applicator tip having a generally convex application surface having an angle θ between 35° and 75° with respect to a centerline of the stone applicator tip for applying the product to a surface and a product delivery passageway extending through the stone applicator tip and terminating in an aperture in the application face, wherein the stone applicator tip comprises engineered stone that has been molded to thereby form the applicator tip.

11. The dispenser of claim 10, wherein the stone applicator tip comprises powdered stone that has been molded to thereby form the applicator tip.

12. The dispenser of claim 10, wherein the stone applicator tip comprises jade.

13. The dispenser of claim 10, wherein the stone applicator tip is fixed to the housing against movement relative to the housing.

14. The dispenser of claim 10, wherein the stone applicator tip comprises a generally convex, disk-shaped body.

15. The dispenser of claim 10, wherein the stone applicator tip comprises a generally curvilinear shape, a generally cylindrical shape, or a generally planar shape.

16. The dispenser of claim 10, wherein the engineered stone comprises marble.

17. A dispenser comprising:

a housing having a reservoir for containing a product; and a unitary stone applicator tip having a generally disk-shape and comprising:

a generally convex application face having an angle θ between 35° and 75° with respect to a centerline of the stone applicator tip for applying a product to a surface, the stone applicator tip being fixedly mounted to the housing; and a delivery passageway configured to convey product from the reservoir to the application face;

wherein the stone applicator tip comprises soapstone, granite, marble, river rock, river stones, pebbles, metallic stone/ores, volcanic stone, engineered/composite stone, or synthetic stone, or composites thereof, whether naturally occurring or synthetic.

18. The dispenser of claim 17, wherein the stone applicator tip comprises marble.

* * * * *